US006217636B1

(12) United States Patent
McFarland

(10) Patent No.: US 6,217,636 B1
(45) Date of Patent: Apr. 17, 2001

(54) TRANSPIRATED WALL AEROSOL COLLECTION SYSTEM AND METHOD

(75) Inventor: Andrew R. McFarland, College Station, TX (US)

(73) Assignee: The Texas A&M University System, College Station, TX (US)

(*) Notice: Subject to any disclaimer, the term of this patent is extended or adjusted under 35 U.S.C. 154(b) by 0 days.

(21) Appl. No.: 09/267,991

(22) Filed: Mar. 12, 1999

Related U.S. Application Data

(60) Provisional application No. 60/078,754, filed on Mar. 13, 1998.

(51) Int. Cl.[7] ................. B01D 45/10; B01D 45/16; B01D 50/00
(52) U.S. Cl. ................. 95/216; 95/219; 95/220; 95/222; 95/227; 96/286; 96/316; 96/327; 96/366; 55/339; 55/465; 73/863.22
(58) Field of Search ................. 96/314, 315, 316, 96/322, 324, 325, 326, 327, 365, 366, 367, 368, 369, 370, 286; 55/462, 465, 339; 95/227, 219, 220, 217, 216, 221, 222; 73/863.21, 863.22

(56) References Cited

U.S. PATENT DOCUMENTS

| 1,888,603 | * | 11/1932 | Mauthe | 96/316 |
| 4,012,209 | * | 3/1977 | McDowell et al. | 96/325 |
| 4,911,233 | * | 3/1990 | Chao et al. | 96/326 |
| 5,011,517 | * | 4/1991 | Cage et al. | 96/316 |
| 5,902,377 | * | 5/1999 | Morgan | 95/218 |
| 5,928,405 | * | 7/1999 | Ranade et al. | 75/337 |
| 6,051,257 | * | 4/2000 | Kodas et al. | 424/489 |

* cited by examiner

Primary Examiner—David A. Simmons
Assistant Examiner—Robert A. Hopkins
(74) Attorney, Agent, or Firm—Baker Botts L.L.P.

(57) ABSTRACT

A transpirated wall aerosol collection system includes a collector operable to receive a gas flow containing particulate matter. The system also includes a porous wall having a first surface and a second surface. The porous wall is operable to transpire a liquid from the first surface to the second surface. Particulate matter contained in the gas flow is deposited in the liquid on the second surface of the porous wall. A virtual impactor may be used with the system for concentrating the particulate matter contained in the gas flow.

21 Claims, 4 Drawing Sheets

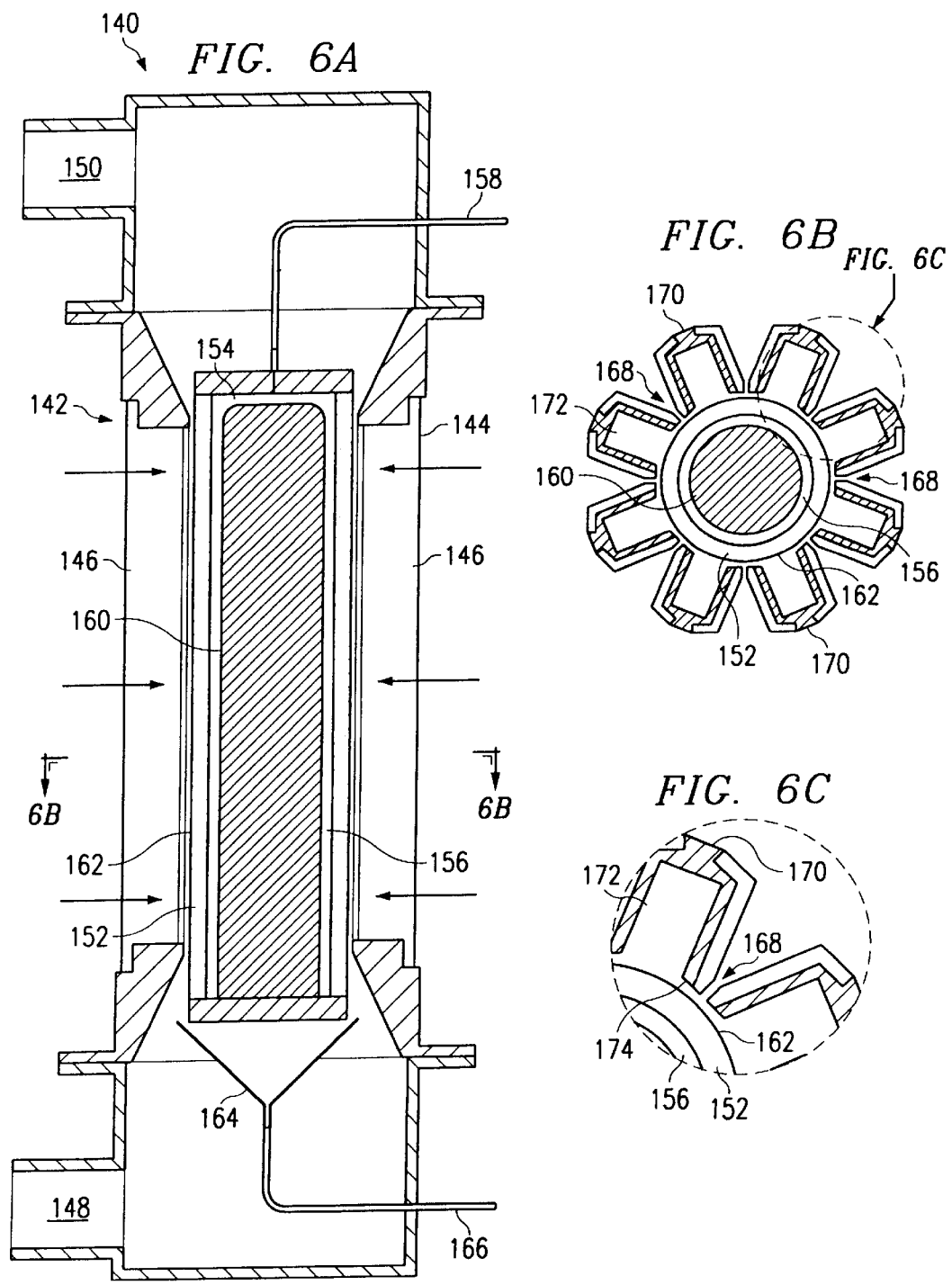

TRANSPIRATED WALL AEROSOL COLLECTION SYSTEM AND METHOD

RELATED APPLICATIONS

This application claims the benefit of Prov. Appl. Ser. No. 60/078,754, entitled "Transpirated Wall Aerosol Collection System and Method", filed provisionally on Mar. 13, 1998.

TECHNICAL FIELD OF THE INVENTION

This invention relates generally to aerosol collection, and more particularly, to a transpirated wall aerosol collection system and method.

BACKGROUND OF THE INVENTION

Aerosol collection devices are used to transfer particulate matter contained in a gas flow onto a solid or liquid surface. One example use of a collection device is in the sampling of biological aerosols, or bioaerosols, where the aerosol collection system is based on jet impaction of aerosols onto a collection plate. The impactor may fractionate the aerosol and deposit size-segregated aerosol particles onto separate agar-filled petri dishes. For example, Graseby Anderson Inc., located in Smyrna, Ga., manufactures a multi-stage impactor that operates at a flow rate of twenty-eight liters per minute and fractionates the aerosol into six size fractions.

Another example of an aerosol collection system used for bioaerosols is a cyclone. A cyclone has been used to collect bioaerosol material from a high flow rate of air, such as approximately 500 liters per minute, into a small flow rate of liquid, generally a few milliliters per minute. Cyclones generally employ an upstream spray of liquid to form a mist. The mist is collected by the cyclone and washes particulate matter collected by the cyclone to a collection location.

SUMMARY OF THE INVENTION

Known systems present certain drawbacks. For example, jet impaction processes generally must be done on a batch basis because the particulate matter is generally not easily removable from the collection surfaces. Further, for example, liquid flow patterns in cyclones often break into rivulets, which reduce the area of the collection surface that is continuously washed. Additionally, cyclones may not be practical in cold weather applications because the liquid mist may freeze and be rendered incapable of continuously wetting the cyclone wall.

Accordingly, a need has arisen for an improved aerosol collection system and method. The present invention provides a transpirated wall aerosol collection system and method that addresses shortcomings of prior systems and methods.

According to one embodiment of the present invention, a transpirated wall aerosol collection system includes a collector operable to receive a gas flow containing particulate matter. The system also includes a porous wall having a first surface and a second surface. The porous wall is for transpiring a liquid from the first surface to the second surface. The liquid on the second surface receives particulate matter contained in the gas flow.

According to another embodiment of the present invention, a method for collecting aerosol includes receiving a gas flow containing particulate matter. The method also includes transpiring a liquid from a first surface to a second surface of a porous wall. The method further includes collecting the particulate matter in the liquid on the second surface of the porous wall using a collector.

The present invention provides several technical advantages. According to an aspect of the invention, liquid may be transpirated through a porous wall to wet a collection surface in a nearly uniform manner, thereby substantially preventing the formation of rivulets. The liquid containing the particulate matter may be removed and analyzed with near-real-time detectors for biological material. The liquid containing the particulate matter may also be stored for subsequent analysis using instrumental means or classical biological analysis techniques, such as culturing the collected biological particles in a nutrient medium. For example, near-real-time analyzers such as flow cytometers and immunoassay devices may be used to process low flow rate liquid samples. The liquid and/or the walls of the collector may be heated, thereby substantially precluding ice formation. Heating the liquid and/or the walls of the collector may also obviate a requirement to heat the gas flow, thereby reducing the energy required to operate the system.

According to another aspect of the present invention, a virtual impactor may be used to concentrate the particulate matter in the gas flow delivered to the transpirated wall particulate collections system. The particulate matter may be collected on a flowing liquid film transpirated through a porous wall. Therefore, the present invention provides greater sensitivity than prior systems by producing a higher concentration of particulate matter in the collected liquid.

According to another aspect of the invention, a jet impactor may be used for collecting the particulate matter. The jet impactor may be used to provide a continuous liquid sample to an analyzer such as an atomic absorption spectrometer.

The present invention may also be used in commercial or industrial applications. For example, a product may initially be in an aerosol state. The product may be collected using the present invention and delivered in hydrosol state for packaging or further processing. Therefore, the present invention provides greater flexibility than prior systems.

According to another aspect of the present invention, a slit impaction system may be used with the present invention. The slit impaction system may include one or more slits through which the gas flow may be accelerated. A transpirated porous wall may be disposed in close proximity to the discharge side of the slits. Particulate matter having sufficient inertia may be deposited in the liquid and be collected for near-real-time analysis or storage. Thus, the present invention provides greater flexibility than prior systems.

Other aspects and technical advantages will be readily apparent to one skilled in the art from the following figures, descriptions, and claims.

BRIEF DESCRIPTION OF THE DRAWINGS

For a more complete understanding of the present invention and the advantages thereof, reference is now made to the following descriptions taken in connection with the accompanying drawings in which:

FIG. 6A is a transpirated wall aerosol collection system in accordance with another embodiment of the present invention;

FIG. 6B is a section view of the transpirated wall aerosol collection system of FIG. 6A taken along the line 6B—6B of FIG. 6A;

FIG. 6C is an enlarged view of a portion of the section view of FIG. 6B; and

DETAILED DESCRIPTION OF THE PREFERRED EMBODIMENTS

Among other things, the present invention incorporates a porous wall into an aerosol collection system. Particulate matter from a subject gas flow is deposited in a liquid film produced by the transpiration of liquid through the porous wall. The system enables near-real-time analysis of the particulate matter contained in the liquid. The liquid containing the particulate matter may also be stored for subsequent analysis.

The preferred embodiments of the present invention are best understood by referring to the following description and drawings, wherein like numerals are used for like and corresponding parts of the various drawings.

Figure 1:
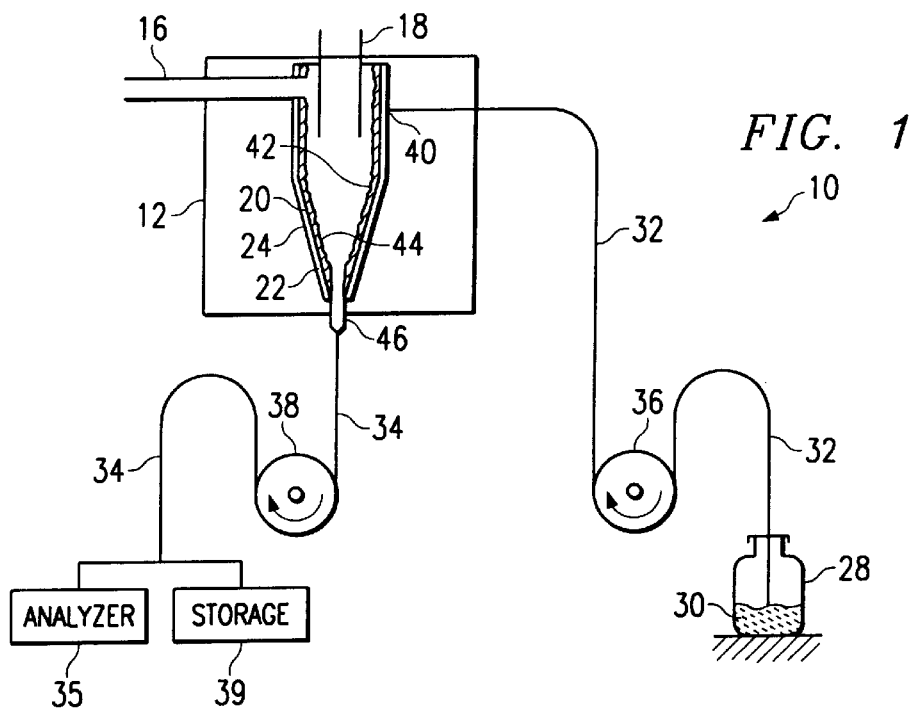
FIG. 1 is a transpirated wall aerosol collection system in accordance with an embodiment of the present invention.

FIG. 1 is a transpirated wall aerosol collection system 10 in accordance with an embodiment of the present invention. System 10 includes a collector 12 for collecting particulate matter contained in a gas or aerosol. In the embodiment illustrated in FIG. 1, collector 12 includes a cyclone. Collector 12 includes a gas inlet 16 and a gas outlet 18. The gas containing the particulate matter enters gas inlet 16 of collector 12 and exits through gas outlet 18. A pump, suction device, or other suitable method or device may be used for directing the gas containing the particulate matter through collector 12.

System 10 also includes a porous wall 20 disposed within collector 12. In this embodiment, collector 12 includes a cyclone. Thus, porous wall 20 is constructed having a generally circular configuration for positioning within collector 12 so that porous wall 20 is disposed adjacent to and in contact with a circular gas flow within collector 12. Porous wall 20 is separated by a gap or plenum 22 from a wall 24 of collector 12. As will be described in greater detail below, a liquid is transpirated through porous wall 20 so that particulate matter contained in the gas may be deposited in the liquid and removed from collector 12. Porous wall 20 may be constructed from sintered stainless steel having a thickness of approximately three millimeters and a 0.5 micrometer pore size. However, porous wall 20 may be constructed from other suitable materials, such as sintered porcelain, porous plastics or other suitable porous metals. Porous wall 20 may also be constructed having other suitable thicknesses and pore sizes. For example, decreasing the pore size of porous wall 20 and/or increasing the thickness of porous wall 20 may require an increased pressure differential across porous wall 20 to produce a continuous liquid film 44 on collection surface 42 of porous wall 20. Further, for example, increasing the pore size of porous wall 20 and/or decreasing the thickness of porous wall 20 may increase the liquid flow through porous wall 20.

As illustrated in FIG. 1, system 10 also includes a reservoir 28 containing a liquid 30. Liquid 30 is delivered from reservoir 28 to collector 12 via a liquid supply line 32. System 10 also includes a receiver line 34 for transporting liquid 30 from collector 12 to an analyzer 35. In the embodiment illustrated in FIG. 1, pumps 36 and 38 are used for delivering liquid 30 to and from collector 12. However, other suitable methods or devices may be used for transporting liquid 30 to and from collector 12. Additionally, liquid 30 may be transported to a storage device 39 via receiver line 34.

In operation, gas containing particulate matter enters gas inlet 16 of collector 12. Liquid 30 enters plenum 22 through a liquid inlet 40 of collector 12 via supply line 32. Due to a pressure differential across porous wall 20, liquid 30 transpires from plenum 22 through porous wall 20 to a collection surface 42 of porous wall 20. Liquid 30 transpiring through porous wall 20 forms a liquid film 44 on collection surface 42. The flow rate of liquid 30 required to form a continuous liquid film 44 on collection surface 42 varies depending on several factors, including the difference in water vapor pressure in the gas and liquid, the size of collector 12, and the gas flow rate. For example, liquid 30 may be transpirated through porous wall 20 to wet collection surface 42 in a nearly uniform manner. However, liquid 30 may also be intermittently transpirated through porous wall 20. The pressure differential required to force liquid 30 through porous wall 20 varies depending upon certain factors, including the pore size of porous wall 20, the desired velocity of liquid 30, and the thickness of porous wall 20. The pressure differential is, however, generally on the order of a few hundred to a few thousand Pascals.

Due to centrifugal forces within collector 12, aerosol particles having aerodynamic diameters larger than approximately one micrometer are deposited in liquid film 44 due to inertial forces acting on the particulate matter. In the embodiment illustrated in FIG. 1, liquid film 44 flows downwardly due to gravitational forces to a liquid outlet 46 where liquid film 44 may be received and delivered to an analyzer 35 or storage device 39 via receiver line 34.

Therefore, aerosol collection system 10 provides greater flexibility than prior aerosol collection systems by allowing near-real-time analysis of particulate matter. Particulate matter contained in liquid 30 may also be stored for subsequent analysis or use. System 10 also provides greater sensitivity than prior systems by providing a greater concentration ratio of particulate matter. For example, a concentration ratio may be defined as the concentration of hydrosol particles to the concentration of aerosol particles. If collector 12 is operated at a gas flow rate of 1000 liters per minute, and has a liquid 30 flow rate of two milliliters per minute, the concentration ratio would be approximately 500,000, provided all particles collected by collector 12 appear in the liquid. Other combinations of liquid and gas flow rates may be used to provide concentration ratios between 100,000 and 1,000,000.

Figure 2:
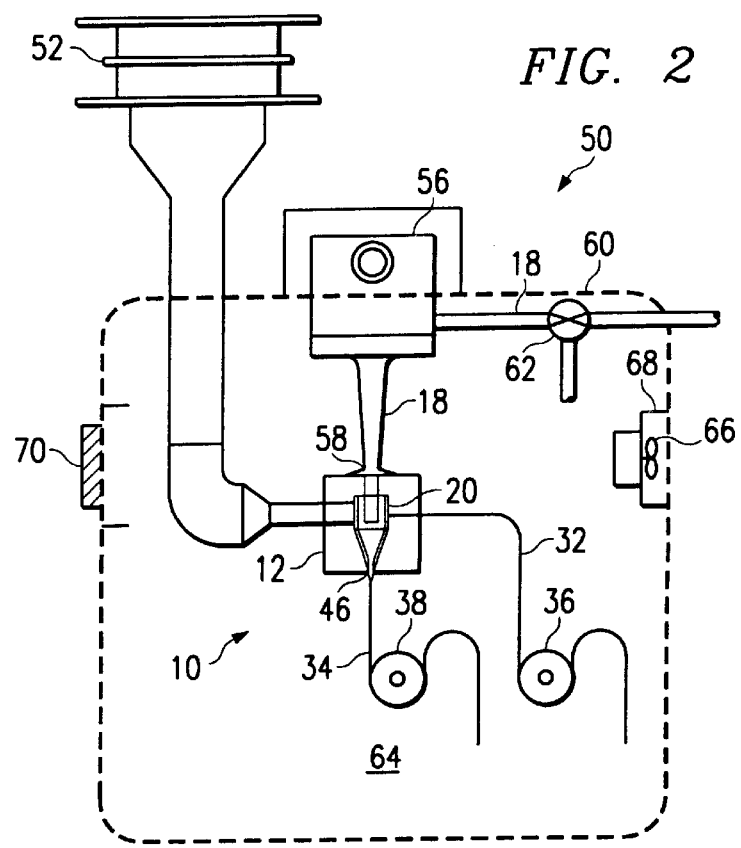
FIG. 2 is an aerosol sampling system incorporating the transpirated wall aerosol collection system of FIG. 1.

FIG. 2 is an aerosol sampling system 50 incorporating transpirated wall aerosol collection system 10 illustrated in FIG. 1. As illustrated in FIG. 2, system 50 includes gas inlet 52 for receiving a gas or aerosol containing particulate matter. System 50 also includes a suction blower 56 and a critical flow venturi 58. As illustrated in FIG. 2, suction blower 56 and critical flow venturi 58 are disposed downstream of collector 12 associated with gas outlet 18. Suction blower 56 and critical flow venturi 58 provide a controlled rate of gas flow through collector 12. For example, suction blower 56 and critical flow venturi 58 may be used to provide a gas flow rate of 1000 liters per minute through collector 12. However, other suitable devices or methods may also be used for providing a controlled rate of gas flow through collector 12.

In operation, a liquid is transported to collector 12 via supply line 32 and is transpirated through porous wall 20. As described above in connection with FIG. 1, particulate matter contained in the gas is deposited in liquid film 44 formed on collection surface 42 of porous wall 20. Referring to FIG. 2, the liquid containing the particulate matter travels downwardly toward liquid outlet 46 and is transported to an analyzer or storage device (not explicitly shown) via receiver line 34. Pumps 36 and 38 for transporting the liquid to and from collector 12 may include separate pump heads attached to a common pump motor. However, other suitable methods or devices may also be used for transporting the liquid to and from collector 12.

As illustrated in FIG. 2, portions of system 50 may be contained within an environmental enclosure 60, thereby providing environmental protection for various components of system 50. System 50 may also include a thermostatically controlled valve 62 associated with gas outlet 18 for diverting a portion of the gas traveling through gas outlet 18 into an internal area 64 of environmental enclosure 60 for heating portions of system 50.

Additionally, system 50 may include a fan 66 for providing heating or cooling to system 50. For example, fan 66 may be used to direct heated or cooled gas into internal area 64 of environmental enclosure 60 from an inlet 68 of environmental enclosure 60 to an outlet 70 of environmental enclosure 60. Therefore, collector 12 and/or the liquid traveling through collector 12 may be heated or cooled to ensure proper operation of system 50 during environmentally adverse operating conditions.

Figure 3:
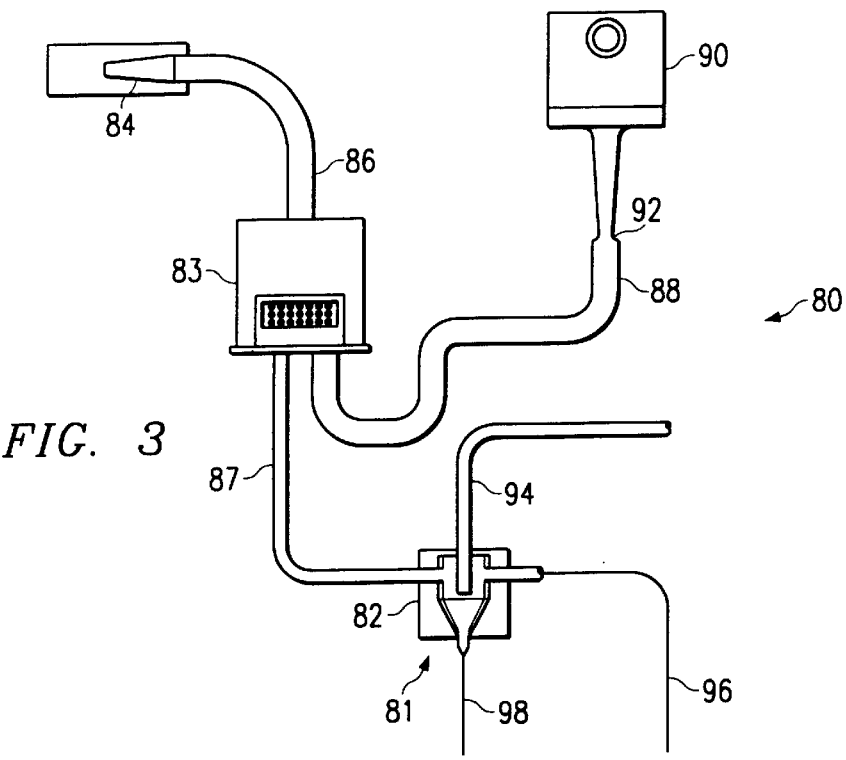
FIG. 3 is an aerosol sampling system incorporating a transpirated wall aerosol collection system in accordance with another embodiment of the present invention.

FIG. 3 is an aerosol sampling system 80 incorporating a transpirated wall aerosol collection system 81 in accordance with an another embodiment of the present invention. As illustrated in FIG. 3, system 81 includes a collector 82 for collecting particulate matter. In this embodiment, collector 82 includes a cyclone having a porous wall disposed within the cyclone as illustrated in FIG. 1. Referring to FIG. 3, system 80 also includes a virtual impactor 83 for concentrating particulate matter contained in a gas for delivery to collector 82. An example of a virtual impactor 83 includes Model No. 340 of MSP Corporation of Minneapolis, Minn.

Gas containing the particulate matter enters an inlet such as a shrouded probe 84 and is transported to virtual impactor 83 via gas inlet 86. For example, the gas may be drawn into virtual impactor 83 at a flow rate of approximately 1050 liters per minute. Virtual impactor 83 separates the gas containing the particulate matter into two streams. A first stream travels via gas inlet 87 to collector 82. For example, the first stream delivered to collector 82 may flow at a rate of fifty-seven liters per minute and contain particulate matter generally larger than approximately one micrometer aerodynamic diameter and comprise approximately five percent of the particulate matter having sizes smaller than approximately one micrometer aerodynamic diameter. A second stream resulting from virtual impactor 83 may be drawn through a gas outlet 88 and discharged from system 80. The second stream may flow at a rate of approximately 993 liters per minute and may contain the remaining particulate matter having sizes approximately less than one micrometer aerodynamic diameter. The combination of virtual impactor 83, operated at a flow rate of approximately 1050 liters per minute, and collector 82 results in a required liquid flow rate through collector 82 of approximately one milliliter per minute, thereby providing a greater concentration of particulate matter in a reduced liquid flow rate. For example, operating virtual impactor 83 at a flow rate of approximately 1050 liters per minute, and transpirating liquid through collector 82 at a flow rate of one milliliter per minute will result in a concentration ratio of approximately 1,000,000. Other combinations of liquid and gas flow rates may also be used to provide concentration ratios of 100,000 to 2,000,000. Additionally, relatively small liquid and/or gas flow rates through system 80 may be heated and/or cooled without expending large amounts of power. Thus, the present invention provides greater efficiency than prior systems.

As illustrated in FIG. 3, system 80 also includes a suction blower 90 and a critical flow venturi 92 associated with gas outlet 88 for providing a controlled rate of gas flow through virtual impactor 83. Additionally, a controlled rate of gas flow through collector 82 may be provided by a pump (not explicitly shown) or other suitable method of device associated with a gas outlet 94 for providing a controlled rate of gas flow through collector 82. As described above in connection with FIGS. 1 and 2, a liquid enters collector 82 via a liquid supply line 96 and is transpirated through a porous wall. Particulate matter having aerodynamic diameters larger than approximately one micrometer is deposited on a liquid film formed on a collection surface of the porous wall. The liquid containing the deposited particulate matter travels downwardly to a liquid outlet and is transported to an analyzer or storage device (not explicitly shown) via a receiver line 98.

Therefore, system 80 provides greater flexibility than prior aerosol sampling systems by allowing concentrated quantities of particulate matter to be delivered to a collector 82 of sampling system 80 for subsequent depositing into a liquid flow for analyzation or storage. Additionally, the addition of virtual impactor 83 allows collector 82 to be constructed having a smaller scale, thereby requiring a reduced liquid flow. For example, virtual impactor 83 provides a concentrated quantity of particulate matter to collector 82 in a reduced gas flow.

Figure 4:
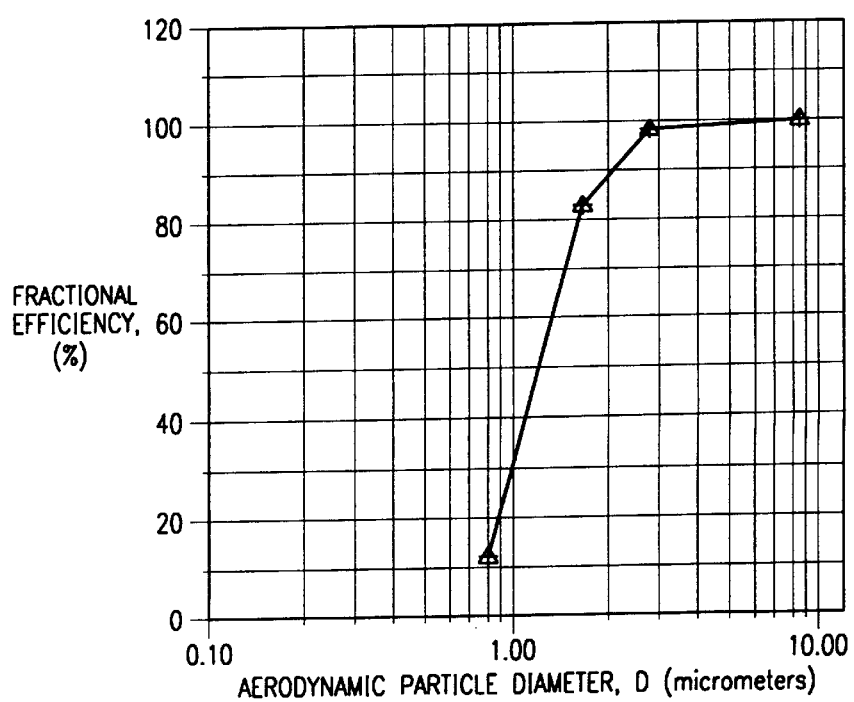
FIG. 4 is a graph illustrating the fractional efficiency of the transpirated wall aerosol collection system of FIG. 3.

FIG. 4 is a graph illustrating the fractional efficiency of transpirated wall aerosol collection system 81 of FIG. 3 for a gas flow rate of approximately fifty-seven liters per minute through collector 82. The cutpoint of collector 82 is approximately one micrometer aerodynamic diameter, where the cutpoint is defined as the size of the particulate matter for which the collection efficiency of collector 82 is approximately fifty percent. For example, bioaerosol particles in the size range of two to ten micrometer aerodynamic diameter may be desired. In this example, the data provided in FIG. 4 illustrates that collector 82 collects approximately ninety-five percent or more of the particulate matter having sizes larger than approximately two micrometer aerodynamic diameter.

Figure 5A:
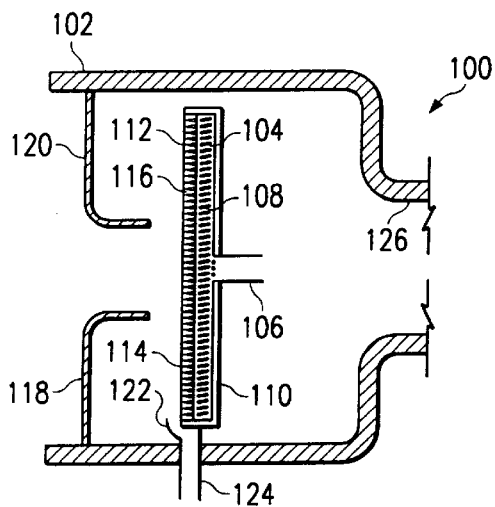
FIG. 5A is a transpirated wall aerosol collection system in accordance with another embodiment of the present invention.

FIG. 5A is a transpirated wall aerosol collection system 100 in accordance with another embodiment of the present invention. System 100 includes a collector 102 for collecting particulate matter contained in a gas. In this embodiment, collector 102 includes a modified jet impactor. An example of jet impactor suitable for modification in accordance with this embodiment is Model No. 10-880 available from Graseby Andersen, Inc. In operation, a liquid 104 is transported via a liquid supply line 106 to a gap or plenum 108 between a wall 110 and a porous wall 112. A pressure differential across porous wall 112 causes liquid 104 to transpirate from plenum 108 to a collection surface 114 of porous wall 112. As liquid 104 transpirates through porous wall 112, a liquid film 116 forms on collection surface 114.

Gas containing particulate matter enters collector 102 at gas inlet 118 and is accelerated by one or more flow nozzles 120 of collector 102 toward collection surface 114. Particulate matter contained in the gas having sufficient inertia are deposited in liquid film 116 on collection surface 114. In the embodiment illustrated in FIG. 5A, liquid film 116 flows downwardly along collection surface 114 due to gravitational forces to a receiver 122 where liquid film 116 containing the particulate matter is transported to an analyzer or storage device (not explicitly shown) via receiver line 124. A vacuum source (not explicitly shown) may be used to draw the gas containing the particulate matter through flow nozzle 120 to a gas outlet 126 of collector 102. However, other suitable devices or methods may be used for drawing the gas through collector 102. Additionally, as described above in connection with FIG. 3, critical flow venturis or other suitable methods or devices may be used to provide a controlled rate of gas flow through collector 102.

Therefore, system 100 provides greater flexibility than prior systems by collecting the particulate matter on a continuously flowing liquid film at a high concentration ratio. For example, collector 102 may be operated at a gas flow rate of twenty-eight liters per minute, and the liquid may be transpirated through porous wall 112 at a flow rate of one milliliter per minute. The resulting concentration ratio would be approximately 280,000. Other gas and liquid flow rate combinations may also be used to provide concentration ratios from 100,000 to 600,000.

Figure 5B:
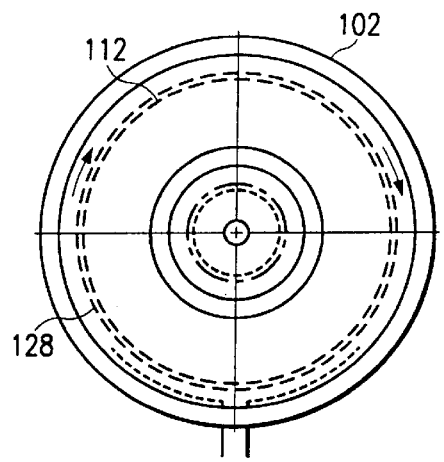
FIG. 5B is a section view of the transpirated wall aerosol collection system of FIG. 5A taken along the line 5B—5B of FIG. 5A.

FIG. 5B is a section view of system 100 of FIG. 5A taken along the line 5B—5B of FIG. 5A. In this embodiment, porous wall 112 may also be rotated so that liquid film 116 containing the particulate matter may be forced, via centrifugal force, to an outer edge 128 of porous wall 112 where liquid film 116 containing the particulate matter may be aspirated using a pump (not explicitly shown) or other suitable method or device. Additionally, as illustrated and described above in connection with FIG. 3, a virtual impactor may also be used for concentrating large-diameter particulate matter into a gas stream for delivery to collector 102 where the particulate matter may be deposited on collection surface 114 and delivered to an analyzer for near-real-time analysis or a storage unit. Particulate matter may also be received by collector 102 from one or more virtual impactors, thereby delivering to collector 102 a concentrated flow of particulate matter.

FIG. 6A is a transpirated wall aerosol collection system 140 in accordance with another embodiment of the present invention. System 140 includes a collector 142 for collecting particulate matter contained in a gas or aerosol. In the embodiment illustrated in FIG. 6A, collector 142 includes a slit impaction system having one or more slit impactors 144. System 140 may include a plurality of gas inlets 146 and gas outlets 148 and 150. In operation, the gas containing the particulate matter enters gas inlets 146 and exits gas outlets 148 and 150. For example, gas entering slit impactor 144 at a location below a midline of slit impactor 144 will be discharged through gas outlet 148, and gas entering slit impactor 144 above the midline of slit impactor 144 will be discharged through gas outlet 150.

System 140 also includes a porous wall 152 acting as a collection surface for each slit impactor 144. In operation, a liquid 154 is delivered to a gap or plenum 156 via liquid supply line 158. An element 160 may be disposed within plenum 156 for reducing the quantity of liquid 154 contained in operating system 140. Element 160 may be a plug or other suitable device. Additionally, element 160 may include a heating element for heating liquid 154 and/or porous wall 152 for maintaining operation of system 140 during environmentally adverse operating conditions.

Due to a pressure differential across porous wall 152, liquid 154 transpires from plenum 156 through porous wall 152 to a collection surface 162 of porous wall 152. Liquid 154 transpiring through porous wall 152 forms a liquid film on collection surface 162. As the gas enters slit impactor 144, the particulate matter contained in the gas is deposited in the liquid film formed on collection surface 162 of porous wall 152. As described above in connection with FIG. 1, the flow rate of liquid 154 required to form a continuous liquid film on collection surface 162 varies depending on a number of factors, including the difference in water vapor pressure between gas and liquid, the gas flow rate, and the size of slit impactor 144. Additionally, the pressure differential required to force liquid 154 through porous wall 152 varies depending upon factors such as the pore size of porous wall 152, the desired velocity of liquid 154, and the thickness of porous wall 152. The pressure differential is, however, generally on the order of a few hundred to a few thousand Pascals.

In the embodiment illustrated in FIG. 6A, the liquid film containing the particulate matter flows downwardly due to gravitational forces to a receiver 164 where the liquid film containing the particulate matter may be transported to an analyzer or storage device (not explicitly shown) via receiver line 166.

FIG. 6B is a section view of system 140 taken along the line 6B—6B of FIG. 6A. As illustrated in FIG. 6B, porous wall 152 and element 160 are constructed having a generally cylindrical configuration. However, other suitable shapes or geometric configurations may be used for porous wall 152 and element 160. For example, porous wall 152 may be constructed having faceted collection surfaces for receiving the particulate matter. Additionally, in this embodiment, collector 142 includes eight impaction slits 168 for receiving the gas flow. In the embodiment illustrated in FIG. 6B, impaction slits 168 include a gap of 0.25 millimeters and a length of 127 millimeters to obtain collection of particulate matter having sizes larger than approximately one micrometer aerodynamic diameter. However, various quantities and sizes of impaction slits 168 may be used for slit impactor 144. Impaction slits 168 are disposed between adjacent dividers 170 that provide vents 172 for allowing the gas entering slit impactor 144 to travel upwardly and downwardly.

FIG. 6C is an enlarged view of a portion of system 140 illustrated in FIG. 6B. As illustrated in FIG. 6C, an exit plane 174 of impaction slit 168 is disposed a predetermined distance from porous wall 152 to facilitate collection of a desired size of particulate matter contained within the gas entering collector 142. For example, exit planes 174 of impaction slits 168 may be disposed approximately 1.25 millimeters from porous wall 152 for collecting particulate matter larger than approximately one micrometer aerodynamic diameter. However, other suitable distances may be used for locating exit planes 174 of impaction slits 168 adjacent porous wall 152 for obtaining the desired size of particulate matter.

For example, where eight impaction slits 168 may be constructed having a 0.25 millimeter gap extending approximately 127 millimeters in length, operating system 140 at a gas flow rate of 500 liters per minute, and transpiring liquid through porous wall 152 at a rate of three milliliters per minute, would provide a concentration ratio of approximately 170,000 and a cutpoint of approximately one micrometer aerodynamic diameter. Other combinations of liquid and gas flow rates may also be used to provide concentration ratios from 80,000 to 500,000.

Figure 7:
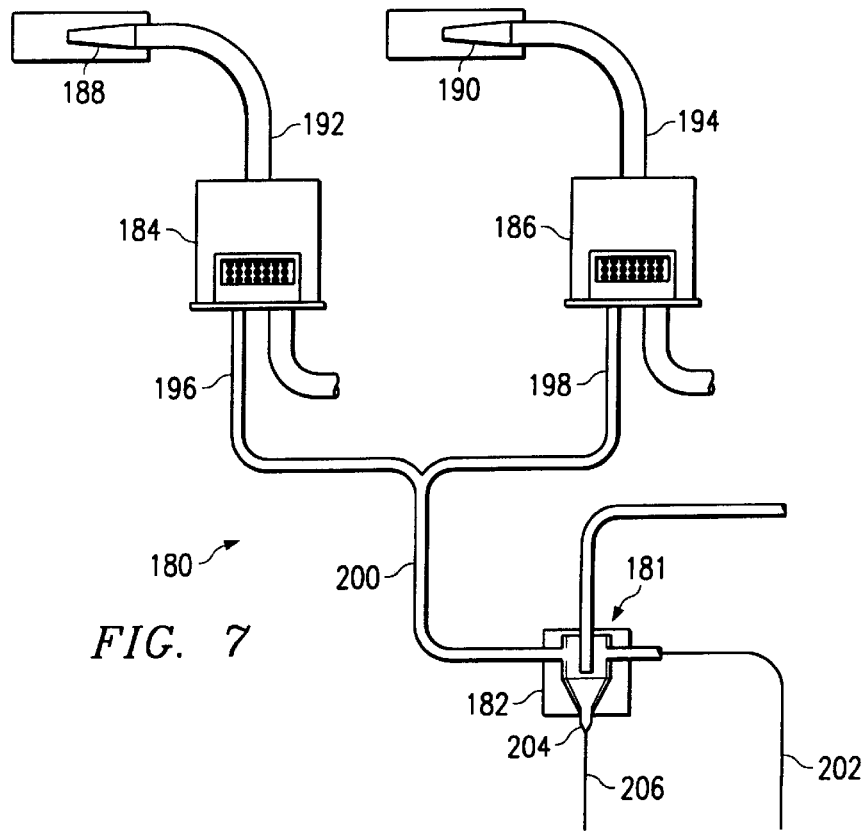
FIG. 7 is an aerosol sampling system incorporating a transpirated wall aerosol collection system in accordance with another embodiment of the present invention.

FIG. 7 is an aerosol sampling system 180 incorporating a transpirated wall aerosol collection system 181 in accordance with another embodiment of the present invention. System 181 includes a collector 182 for collecting particulate matter contained in a gas flow. In this embodiment, collector 182 includes a cyclone having a porous wall disposed within the cyclone as illustrated in FIG. 1. Referring to FIG. 7, system 180 also includes virtual impactors 184 and 186. Virtual impactors 184 and 186 are coupled together and may be operated in parallel.

In operation, the gas flow containing the particulate matter enters inlets such as shrouded probes 188 and 190 and travels towards virtual impactors 184 and 186 via gas inlets 192 and 194, respectively. As described above in connection with FIG. 3, each virtual impactor 184 and 186 separates the gas flow into two streams, thereby providing a greater concentration of particulate matter to collector 182. The concentrated gas flows from virtual impactors 184 and 186 are transported via gas outlets 196 and 198, respectively, to gas inlet 200, where the gas flows are joined and drawn into collector 182.

As described above in connection with FIGS. 1 through 3, a liquid enters collector 182 via a liquid supply line 202 and is transpirated through a porous wall disposed within collector 182. Particulate matter contained in the gas flow is deposited in the liquid transpirating through the porous wall and travels downwardly within collector 182 toward a liquid outlet 204. The liquid is transported to an analyzer or storage device from liquid outlet 204 via a liquid receiver line 206. Thus, the present invention provides greater flexibility than prior systems by allowing a plurality of virtual impactors to be operated with an embodiment of the present invention, thereby accommodating high air flow rates and providing greater particulate concentrations.

Although the present invention and its advantages have been described in detail, it should be understood that various changes, substitutions, and alterations can be made therein without departing from the spirit and scope of the present invention as defined by the appended claims.

What is claimed is:

1. A transpirated wall aerosol collection system comprising:
    a plurality of virtual impactors, the plurality of virtual impactors coupled in parallel for concentrating particulate matter in a gas flow;
    a collector operable to receive the gas flow containing particulate matter from the virtual impactors; and
    a porous wall disposed in the collector, the porous wall having a first surface and a second surface, the porous wall adapted to transpirate a liquid from the first surface to the second surface, wherein when the liquid is transpirated to the second surface, the liquid may receive particulate matter contained in the gas flow.

2. The system of claim 1, wherein the virtual impactors are operable to provide the cyclone with particulate matter having a size of approximately 1 μm or greater.

3. The system of claim 1, wherein the collector comprises a jet impactor.

4. The system of claim 3, wherein the porous wall is disposed within the jet impactor.

5. The system of claim 1, wherein the collector comprises a slit impaction system.

6. The system of claim 5, wherein the slit impaction system comprises a plurality of impaction slits disposed adjacent the porous wall, the impaction slits for receiving the gas flow.

7. The system of claim 1, further comprising a critical flow venturi for controlling the rate of the gas flow through the collector.

8. A transpirated wall aerosol collection system comprising:
    a collector operable to receive a gas flow containing particulate matter, wherein the collector comprises a cyclone; and
    a porous wall having a first surface and a second surface, wherein the porous wall is disposed within the cyclone, the porous wall adapted to transpirate a liquid from the first surface to the second surface, wherein when the liquid is transpirated to the second surface, the liquid may receive particulate matter contained in the gas flow, and wherein the cyclone receives the gas flow from a plurality of virtual impactors, the plurality of virtual impactors coupled in parallel for concentrating the particulate matter in the gas flow.

9. A method for collecting an aerosol comprising:
    receiving a gas flow containing particulate matter in a plurality of virtual impactors, the plurality of virtual impactors coupled in parallel for concentrating the particulate matter in the gas flow;
    receiving the gas flow containing particulate matter from the virtual impactors within a collector;
    transpiring a liquid from a first surface to a second surface of a porous wall, the porous wall disposed within the collector; and
    collecting the particulate matter in the liquid on the second surface of the porous wall.

10. The method of claim 9, and further comprising heating the liquid.

11. The method of claim 10, and further comprising heating the collector.

12. The method of claim 9, and further comprising:
    rotating the porous wall to cause the liquid on the second surface to flow toward an outer edge of the porous wall; and
    aspirating the liquid containing the particulate matter.

13. The method of claim 9, further comprising accelerating the gas flow toward the porous wall, and wherein the collecting step comprises collecting particulate matter in the liquid on the second surface of the porous wall using a jet impactor.

14. The method of claim 9, wherein receiving the gas flow within the collector comprises receiving the gas flow containing particulate matter through a plurality of impaction slits of a slit impaction system.

15. The method of claim 9, further comprising transporting the liquid containing the particulate matter to an analyzer.

16. The method of claim 9, further comprising controlling the rate of the gas flow through the collector using a venturi.

17. A method for collecting an aerosol comprising:
    disposing a collector within an environmental enclosure;
    receiving a gas flow containing particulate matter within the collector;
    transpiring a liquid from a first surface to a second surface of a porous wall, the porous wall disposed within the collector; and
    diverting a portion of the gas flow exhausted from the collector to an internal area of the enclosure.

18. A transpirated wall aerosol collection system comprising:
    a plurality of virtual impactors, the plurality of virtual impactors coupled in parallel for concentrating particulate matter in a gas flow;
    a housing operable to receive the gas flow from the virtual impactors;

a porous wall disposed within the housing, the porous wall having a first side and a second side, the first side exposed to a liquid, the second side exposed to a gas containing particulate matter;

the porous wall adapted to transpirate the liquid from the first side to the second side to form a liquid film on the second side for receiving therein a portion of the particulate matter from the gas.

19. The system of claim 18, further comprising an environmental enclosure, wherein the housing is disposed within the environmental enclosure.

20. A transpirated wall aerosol collection system comprising:

a housing;

a porous wall disposed within the housing, the porous wall having a first side and a second side, the first side exposed to a liquid, the second side exposed to a gas containing particulate matter, the porous wall adapted to transpirate the liquid from the first side to the second side to form a liquid film on the second side for receiving therein a portion of the particulate matter from the gas; and an environmental enclosure, wherein the housing is disposed within the environmental enclosure, and wherein at least a portion of the gas flow exiting the housing is transferred to an internal area of the environmental enclosure.

21. The system of claim 18, further comprising a heater operable to heat the liquid transpiring through the porous wall.

* * * * *